United States Patent
Campin et al.

(10) Patent No.: US 12,076,085 B2
(45) Date of Patent: Sep. 3, 2024

(54) METHOD AND SYSTEM FOR MEASURING OPTICAL PARAMETERS

(71) Applicant: Alcon Inc., Fribourg (CH)

(72) Inventors: John Alfred Campin, Southlake, TX (US); Martin Gruendig, Rangsdorf (DE); Christopher Sean Mudd, Lake Forest, CA (US); George Hunter Pettit, Fort Worth, TX (US); Peter Zieger, Berlin (DE)

(73) Assignee: Alcon Inc., Fribourg (CH)

( * ) Notice: Subject to any disclaimer, the term of this patent is extended or adjusted under 35 U.S.C. 154(b) by 420 days.

(21) Appl. No.: 17/113,611

(22) Filed: Dec. 7, 2020

(65) Prior Publication Data

US 2021/0173229 A1 Jun. 10, 2021

Related U.S. Application Data

(60) Provisional application No. 63/006,820, filed on Apr. 8, 2020, provisional application No. 62/945,909, filed on Dec. 10, 2019.

(51) Int. Cl.
*A61B 3/10* (2006.01)
*A61B 3/14* (2006.01)

(52) U.S. Cl.
CPC ............ *A61B 3/101* (2013.01); *A61B 3/1005* (2013.01); *A61B 3/14* (2013.01)

(58) Field of Classification Search
CPC .......... A61B 3/101; A61B 3/14; A61B 3/1015
USPC ........................................ 351/206, 246, 209
See application file for complete search history.

(56) References Cited

U.S. PATENT DOCUMENTS

| | | | |
|---|---|---|---|
| 7,458,683 B2 * | 12/2008 | Chernyak | A61B 3/0025 351/205 |
| 10,201,276 B2 | 2/2019 | Neal et al. | |
| 2014/0125949 A1 * | 5/2014 | Shea | A61B 3/103 351/205 |
| 2016/0000318 A1 * | 1/2016 | Copland | A61B 5/1103 351/208 |

FOREIGN PATENT DOCUMENTS

WO 2012154278 A1 11/2012
WO WO-2021116885 A1 * 6/2021 ........... A61B 3/0025

* cited by examiner

*Primary Examiner* — Zachary W Wilkes

(57) ABSTRACT

A method of verifying ophthalmic measurements includes obtaining, via an ophthalmic measurement device, a first measurement of at least one ophthalmic parameter over a first measurement area. The first measurement area corresponds to an unassisted visible area of a patient's eye. A second measurement of the at least one ophthalmic parameter over a second measurement area is obtained via the measurement device. The second measurement area corresponds to an assisted visible area of the patient's eye. The first measurement is compared to the second measurement. It is determined if the second measurement diverges from the first measurement. Responsive to a determination that the second measurement diverges from the first measurement, an alert that the second measurement is inaccurate is generated. Responsive to a determination that the second measurement does not diverge from the first measurement, the second measurement is accepted as accurate.

12 Claims, 5 Drawing Sheets

METHOD AND SYSTEM FOR MEASURING OPTICAL PARAMETERS

TECHNICAL FIELD

The present disclosure relates generally to methods and systems for measuring optical parameters of the eye and more particularly, but not by way of limitation, to a method and system for measuring optical parameters that minimizes an impact of distortions resulting from manual opening of an eyelid.

BACKGROUND

This section provides background information to facilitate a better understanding of the various aspects of the disclosure. It should be understood that the statements in this section of this document are to be read in this light, and not as admissions of prior art.

When performing optical measurements on patients it is often important that the patient's eyelid is sufficiently open. Such optical measurements are common, for example, when measuring topography or wavefront as part of a diagnostic exam to obtain data required for subsequent surgery, or just to characterize the eyes as part of a diagnostic workup.

It is quite common that a patient's eyelid does not open sufficiently to allow for data capture over the required area. This is frequently due, for example, to the patient's age or injury to the eye or the surrounding area. In these cases the device operator often manually assists the patient with opening the eyelid. Sometimes, depending upon the level of challenge and ease of access to the eye, a second operator assists.

When opening the eyelid manually, it is possible to inadvertently distort the globe of the eye. This can result in the ensuing measurement being incorrect. Measurements, for example, of astigmatism or higher order aberrations can be particularly impacted. Inaccurate measurements can have a negative impact on any surgical procedure including, for example, intra-ocular lens implantation or corneal refractive surgery. Operators are trained in the best technique so as to minimize potential distortions. However, there is variation between operators and manual manipulation of the eyelid can be challenging for even the most experienced operators with particularly challenging patients. Additionally, when the opening of the patient's eyelid is assisted manually or mechanically, the tear film associated with the patient's cornea often dries due to the patient being unable to blink. Drying of the tear film also leads to inaccurate ophthalmic measurements.

SUMMARY

Various aspects of the disclosure relate to a method of verifying ophthalmic measurements. The method includes obtaining, via an ophthalmic measurement device, a first measurement of at least one ophthalmic parameter over a first measurement area. The first measurement area corresponds to an unassisted visible area of a patient's eye. A second measurement of the at least one ophthalmic parameter over a second measurement area is obtained via the measurement device. The second measurement area corresponds to an assisted visible area of the patient's eye. The first measurement is compared to the second measurement. It is determined if the second measurement diverges from the first measurement. Responsive to a determination that the second measurement diverges from the first measurement, an alert that the second measurement is inaccurate is generated. Responsive to a determination that the second measurement does not diverge from the first measurement, the second measurement is accepted as accurate. First reflections associated with the first measurement and second reflections associated with the second measurement are obtained using the ophthalmic measurement device. The first reflections are compared to the second reflections. It is then determined if there are discrepancies between the first reflections and the second reflections. Responsive to a determination that discrepancies are present between the second reflections and the first reflections, generating an alert that the patient's tear film has dried. Responsive to a determination that there are no discrepancies between the second reflections and the first reflections, accepting the second measurement as accurate.

Various aspects of the disclosure relate to a computer-program product comprising a non-transitory computer-usable medium having computer-readable program code embodied therein. The computer-readable program code adapted to be executed to implement a method that includes receiving, from an ophthalmic measurement device, a first measurement of at least one ophthalmic parameter over a first measurement area. The first measurement area corresponds to an unassisted visible area of a patient's eye. A second measurement of the at least one ophthalmic parameter over a second measurement area is received from the measurement device. The second measurement area corresponds to an assisted visible area of the patient's eye. The first measurement is compared to the second measurement. It is determined if the second measurement diverges from the first measurement. Responsive to a determination that the second measurement diverges from the first measurement, an alert is generated that the second measurement is inaccurate. Responsive to a determination that the second measurement does not diverge from the first measurement, the second measurement is accepted as accurate. First reflections associated with the first measurement and second reflections associated with the second measurement are received from the ophthalmic measurement device. It is determined if there are discrepancies between the first reflections and the second reflections. Responsive to a determination that discrepancies are present between the second reflections and the first reflections, generating an alert that the patient's tear film has dried. Responsive to a determination that there are no discrepancies between the second reflections and the first reflections, accepting the second measurement as accurate.

Various aspects of the disclosure relate to a system for ophthalmic measurement. The system includes an ophthalmic measurement device. A processor is coupled to the ophthalmic measurement device. The processor is configured to receive, from an ophthalmic measurement device, a first measurement of at least one ophthalmic parameter over a first measurement area. The first measurement area corresponds to an unassisted visible area of a patient's eye. A second measurement of the at least one ophthalmic parameter over a second measurement area is received from the ophthalmic measurement device. The second measurement area corresponds to an assisted visible area of the patient's eye. The first measurement is compared to the second measurement and it is determined if the second measurement diverges from the first measurement. Responsive to a determination that the second measurement diverges from the first measurement, generate an alert that the second measurement is inaccurate. Responsive to a determination that the second measurement does not diverge from the first measurement, accept the second measurement as accurate. The processor is configured to receive, from the ophthalmic measurement device, first reflections associated with the first measurement and second reflections associated with the second measurement. It is determined if there are discrepancies between the first reflections and the second reflections. Responsive to a determination that discrepancies are present between the second reflections and the first reflections, an alert that the patient's tear film has dried is generated. Responsive to a determination that there are no discrepancies between the second reflections and the first reflections, the second measurement is accepted as accurate.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion.

DETAILED DESCRIPTION

Various embodiments will now be described more fully with reference to the accompanying drawings. The disclosure may, however, be embodied in many different forms and should not be construed as limited to the embodiments set forth herein.

Prior to medical interventions on the eye, such as for example refractive surgery, retinal surgery, or lens-replacement surgery, it is common for many ophthalmic parameters, such as for example, corneal curvature (also known as keratometry), axial length, aberrometry, corneal anterior surface measurement (also known as corneal topography), or full-thickness measurement of a corneal structure (also known as corneal tomography) to be measured. These ophthalmic parameters are typically measured with specialized equipment and require that a certain minimum surface area of the anterior portion of the eye be visible. In the particular case of lens-replacement surgery, measurement of these ophthalmic parameters dictates the optical properties of a replacement lens. Thus, inaccuracies in measurements of the ophthalmic parameters can adversely impact the efficacy of any such medical intervention on the eye.

Figure 1:
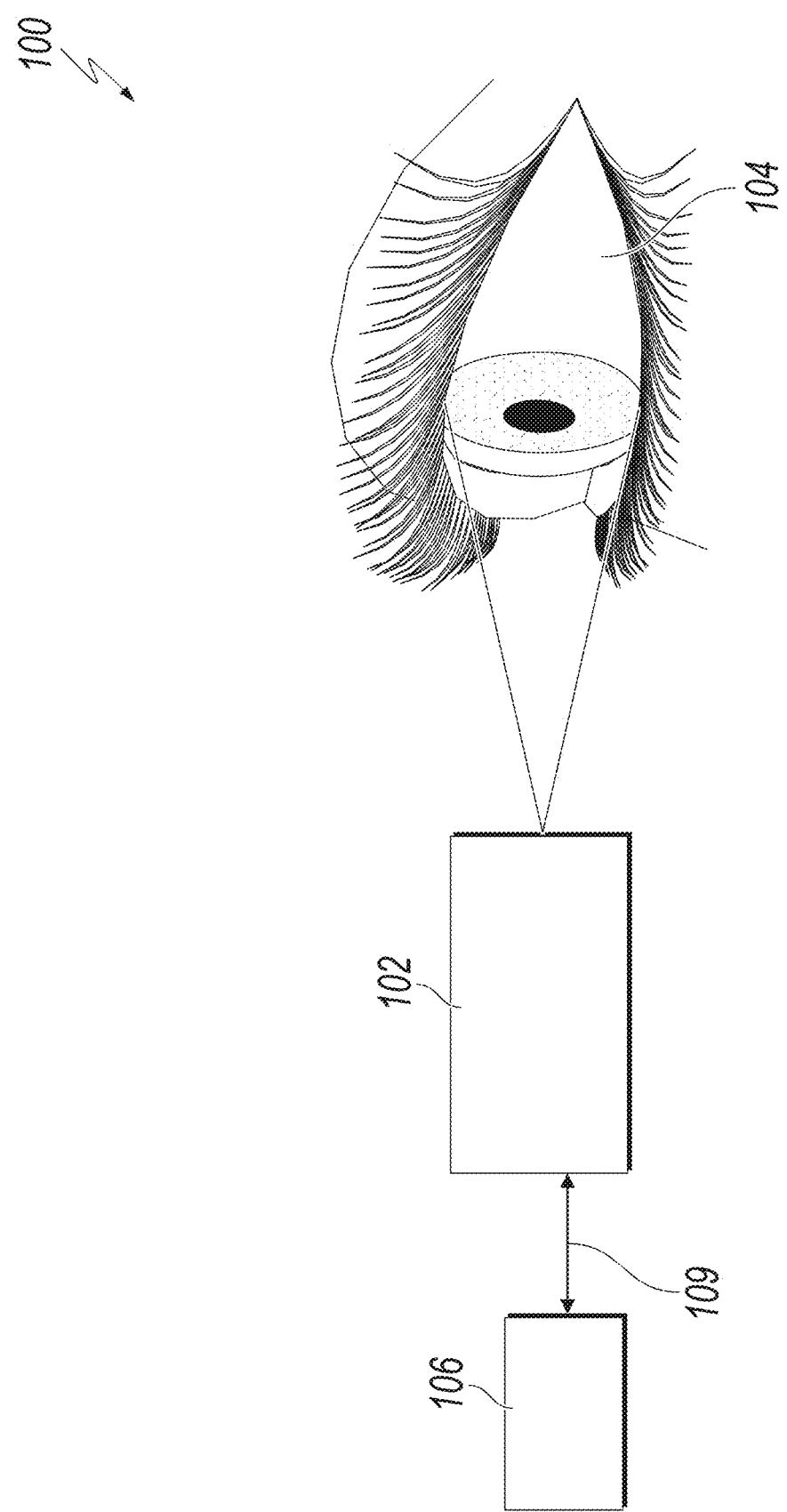
FIG. 1 is a block diagram of an ophthalmic measurement system according to aspects of the disclosure.

FIG. 1 is a block diagram of an ophthalmic measurement system 100. The measurement system 100 includes a measurement device 102 that is positioned to visualize a patient's eye 104. In various embodiments, the measurement device may be any ophthalmic measurement device such as, for example, a keratometer, an ultrasound biometer, a wavefront device, a topographer, an aberrometry device, an ophthalmic optical coherence tomography (OCT) device, or any other ophthalmic measurement device. The measurement device 102 includes a processor 106 that is configured to store and compare the ophthalmic parameters obtained by the measurement device 102. In various embodiments, the processor 106 may be integral with the measurement device 102; however, in other embodiments, the processor 106 may be a stand-alone device that is coupled to the measurement device 102 via, for example, a wired or wireless coupling. The processor 106 may be any microprocessor, microcontroller, programmable element, or other device or collection of devices for processing instructions for the control of the measurement device 102.

In some embodiments, a data bus 109, which in the illustrated embodiment is a serial bus, couples various components of the measurement device 102 together such that data is communicated therebetween. In a typical embodiment, the data bus 109 may include, for example, any combination of hardware, software embedded in a computer readable medium, or encoded logic incorporated in hardware or otherwise stored (e.g., firmware) to couple components of the measurement device 102 to each other. As an example and not by way of limitation, the data bus 109 may include an Accelerated Graphics Port (AGP) or other graphics bus, a Controller Area Network (CAN) bus, a front-side bus (FSB), a HYPERTRANSPORT (HT) interconnect, an INFINIBAND interconnect, a low-pin-count (LPC) bus, a memory bus, a Micro Channel Architecture (MCA) bus, a Peripheral Component Interconnect (PCI) bus, a PCI-Express (PCI-X) bus, a serial advanced technology attachment (SATA) bus, a Video Electronics Standards Association local (VLB) bus, or any other suitable bus or a combination of two or more of these. In various embodiments, the data bus 109 may include any number, type, or configuration of data buses 109, where appropriate.

Figure 2:
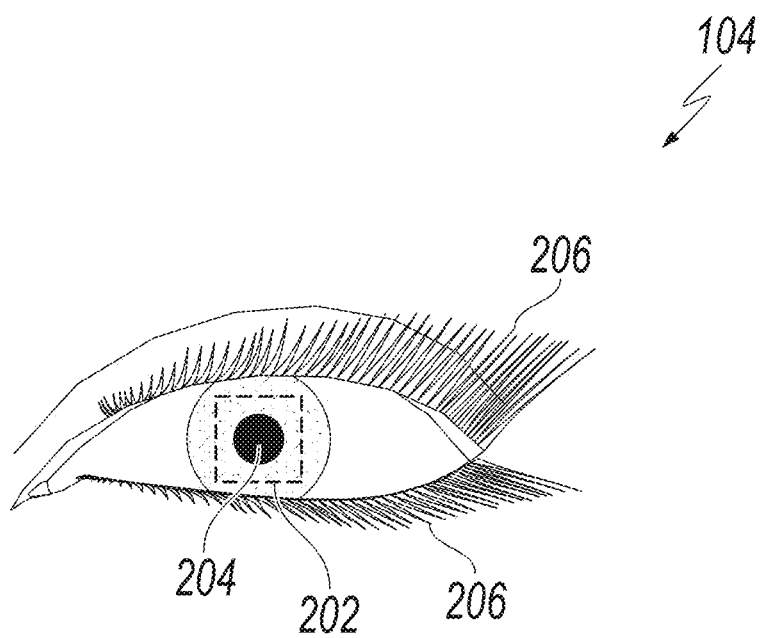
FIG. 2 is a front view of the eye with unassisted lid opening and illustrating a first measurement area.

FIG. 2 is a front view of the eye 104 with unassisted opening of an eyelid 206 and illustrating a first measurement area 202. In a typical embodiment the first measurement area 202 may be, for example, a small diameter around a pupil 204 or a small diameter around some other reference such as, for example, a visual axis or line of sight. Visualization of the first measurement area 202 is often possible without any manual manipulation of the eyelid 206.

Figure 3:
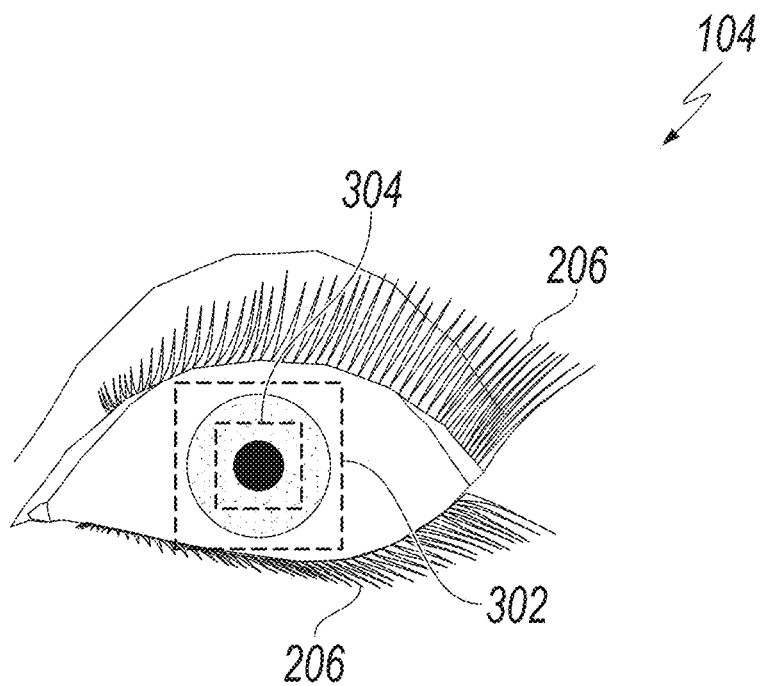
FIG. 3 is a front view of the eye with assisted lid opening and illustrating a second measurement area.

FIG. 3 is a front view of the eye 104 with assisted opening of the eyelid 206 and illustrating a second measurement area 302. The second measurement area 302 is larger than, and encompasses, the first measurement area 202. Specifically, the second measurement area 302 includes a sub-region 304 that coincides with the first measurement area 202. Additionally, the second measurement area 302 includes regions of the eye that would be obscured during unassisted opening of the eyelid 206. If the patient is able to open the eye fully without assistance, then aberrations such as, for example, defocus, astigmatism, or higher order aberrations over the portion of the sub-region 304 of the second measurement area 302 will be similar to the ophthalmic parameters measured over the first measurement area 202 alone. Thus, any divergence in the ophthalmic parameters measured over the second measurement area 302 and the ophthalmic parameters measured over the first measurement area 202 could be indicative of inadvertent deformation of the globe of the eye including, for example, deformation caused by manual opening of the eyelid 206.

It should be noted that the first measurement area 202 and the second measurement area 302 illustrated in FIGS. 2-3 are exemplary only. During operation, the location, size, and shape of the first measurement area 202 and the second measurement area 302 will vary depending on the ophthalmic parameter that is being measured. For example, in FIGS. 2-3, the first measurement area 202 and the second measurement area 302 are illustrated by way of example as being centered on the pupil 204. In various embodiments, the first measurement area 202 and the second measurement area 302 could, for example, be offset from the pupil 204 or may be located elsewhere on the eye 104 so as to include the sclera, iris, or other regions of the eye 104.

Referring to FIGS. 1-3 collectively, during operation, a first measurement of one or more ophthalmic parameters is taken over the first measurement area 202 and transmitted to the processor 106. The ophthalmic parameters are measured over the first measurement area 202 without assistance opening the eyelid 206 being provided to the patient. Assistance is then provided to facilitate the patient opening the eyelid 206 to a greater degree than otherwise possible without assistance. A second measurement of the same ophthalmic parameters is taken over the second measurement area 302 and transmitted to the processor 106. The processor 106 compares the second measurement to the first measurement. In various embodiments, the processor 106 may scale up the range of the ophthalmic parameters measured over the first measurement area 202 to match the range of the second measurement area 302. This practice is commonly known as "data scaling" or "feature scaling." In other embodiments, the processor 106 may sample the ophthalmic parameters measured over the sub-region 304 of the second measurement area 302 and compare the ophthalmic parameters of the sub-region 304 with the ophthalmic parameters measured over the first measurement area 202 alone. This practice is commonly known as "data sampling." In various embodiments, the processor 106 compares the second measurement to the first measurement to assess a consistency of a shape of the eye 104. Such a comparison, in various embodiments, may be accomplished through, for example, a root-mean-square analysis of the ophthalmic parameters. In various embodiments, the processor 106 may utilize registration data in an effort to determine where on the eye 104 the ophthalmic parameters were measured. Such registration data facilitates determination of a common reference between the first measurement area 202 and the second measurement area 302.

Still referring to FIGS. 1-3, if the processor 106 detects no divergence between the ophthalmic parameters measured over the first measurement area 202 and the ophthalmic parameters measured over the second measurement area 302, then no action is taken and processor 106 determines that the ophthalmic parameters measured over the second measurement area 302 are accurate. If the processor 106 detects divergence between the ophthalmic parameters measured over the first measurement area 202 and the ophthalmic parameters measured over the second measurement area 302, then the processor 106 generates an alert notifying the operator of possible deformation of the globe of the eye 104 causing the ophthalmic parameters measured over the second measurement area 302 to be inaccurate. In various embodiments, the alert may be, for example, a visual indication, a textual indication, or an auditory indication. The alert prompts the clinician to examine the assistance provided to the patient's eyelid 206 and re-measure the ophthalmic parameters over the second measurement area 302.

Still referring to FIGS. 1-3, during operation, the ophthalmic parameters may, in various embodiments, include reflections received from the first measurement area 202 and the second measurement area 302. The processor 106 compares reflections detected from the first measurement area 202 and reflections detected from the second measurement area 302. Specifically, the processor determines if blurring or other changes to the reflections have occurred between the first measurement taken over the first measurement area 202 and the second measurement taken over second measurement area 302. Such a change in reflections between the first measurement and the second measurement could be indicative of drying of the patient's tear film. In response to such a determination, the patient's eye should be irrigated or otherwise moistened to replenish the tear film in an effort to ensure accurate measurement of ophthalmic parameters. Additionally, the processor determines if there is an absence of reflections between the first measurement taken over the first measurement area 202 and the second measurement taken over the second measurement area 302. An absence of reflections indicates obstruction or other interference with the signal from the measurement device 102. In various embodiments, the signal may be, for example, visible light emitted from, for example, a light-emitting diode (LED). In other embodiments, the signal may be, for example, a laser emitted from, for example, an optical coherence tomography (OCT) device or a wavefront device. Such an absence of reflections could be indicative, for example, of a need to reposition the devices assisting with opening of the patient's eyelid.

Figure 4:
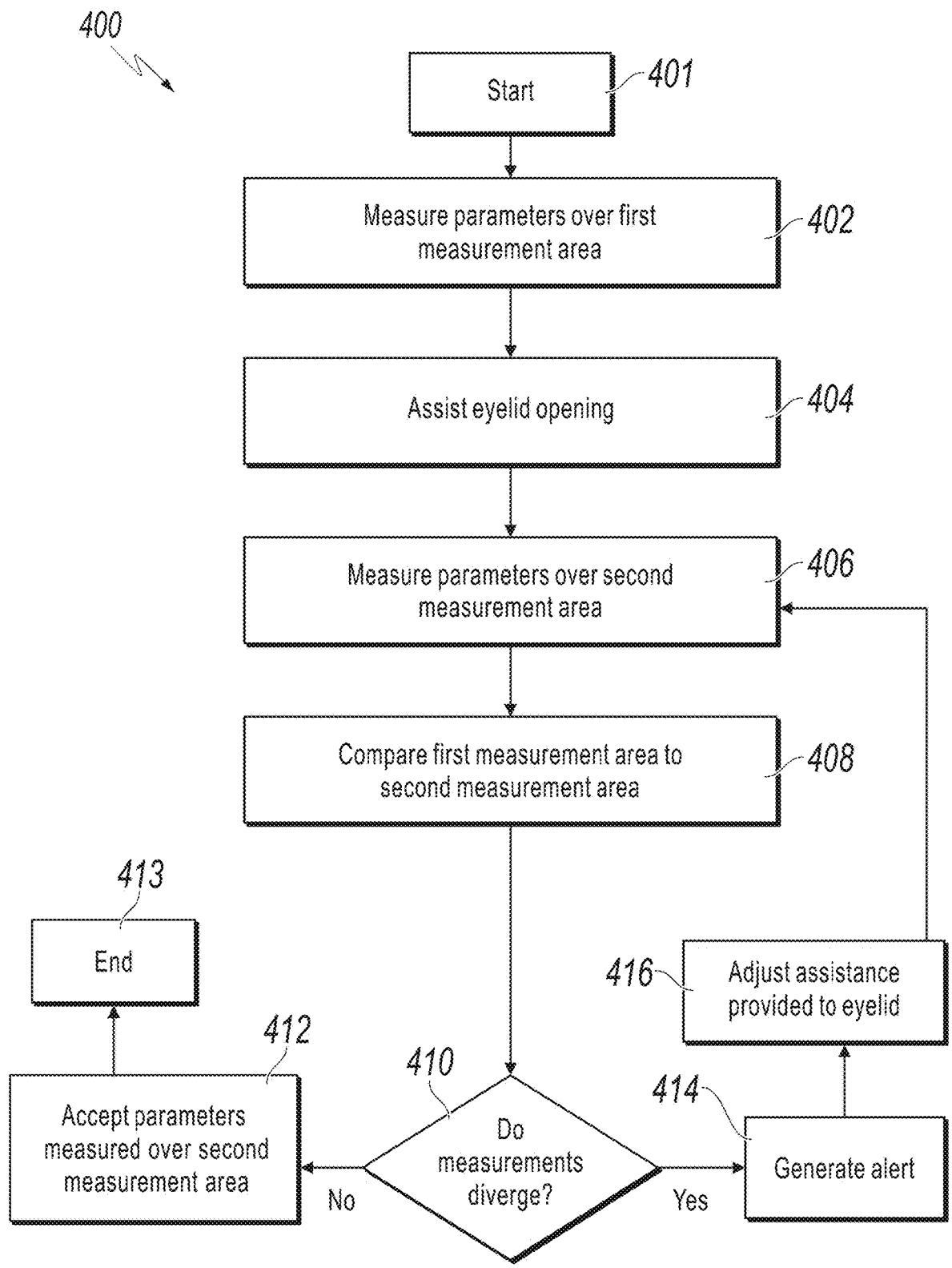
FIG. 4 is a flow diagram of a process for verifying optical measurements according to aspects of the disclosure.

FIG. 4 is a flow diagram of a process 400 for verifying ophthalmic measurements. The process 400 begins at step 401. At step 402, the ophthalmic parameters are measured over the first measurement area 202 and the measured ophthalmic parameters are transmitted to the processor 106. During step 402, the opening of the patient's eyelid 206 is not assisted. At step 404, assistance is provided to open the patient's eyelid 206 thereby opening the eyelid 206 to a degree sufficient to expose the second measurement area 302. At step 406, the ophthalmic parameters are measured over the second measurement area 302 and the measured ophthalmic parameters are transmitted to the processor 106. At step 408, the processor 106 compares the ophthalmic parameters measured over the first measurement area 202 with the ophthalmic parameters measured over at least one of the second measurement area 302 or the sub-region 304 of the second measurement area 302. In step 408, the comparison may, in various embodiments, utilize data scaling such that the ophthalmic parameters measured over the first measurement area 202 are scaled up and compared to the ophthalmic parameters measured over the second measurement area 302. In other embodiments, the comparison may utilize data sampling such that the sub-region 304 is sampled from the ophthalmic parameters measured over the second measurement area 302 and compared to the ophthalmic parameters measured over the first measurement area 202.

Still referring to FIG. 4, at step 410, it is determined if the ophthalmic parameters measured over the first measurement area 202 diverge from the ophthalmic parameters measured over the sub-region 304 of the second measurement area 302. If, at step 410, it is determined that there is no divergence between the ophthalmic parameters measured over the first measurement area 202 and the ophthalmic parameters measured over the sub-region 304 of the second measurement area 302, then the process 400 proceeds to step 412. At step 412, the processor 106 accepts the ophthalmic parameters measured over the second measurement area 302 as accurate. From step 412, the process 400 ends at step 413. In various embodiments, the process 400 may be repeated, for example, with measurements of different ophthalmic parameters or on different anatomical regions of the eye 104.

Still referring to FIG. 4, if at step 410, it is determined that the ophthalmic parameters measured over the first measurement area 202 diverge from the ophthalmic parameters measured over the sub-region 304 of the second measurement area 302, then the process 400 proceeds to step 414. At step 414, the processor 106 generates an alert that the ophthalmic parameters measured over the second measurement area 302 may be inaccurate due to, for example, deformation of the globe of the eye caused by the assistance provided to the patient's eyelid 206. In step 414, the alert may be, for example, a visual indication, a textual indication, or an auditory indication. At step 416, the clinician adjusts the assistance provided to the patient's eyelid 206. From step 416, the process 400 returns to step 406 where the ophthalmic parameters are re-measured over the second measurement area 302.

Figure 5B:
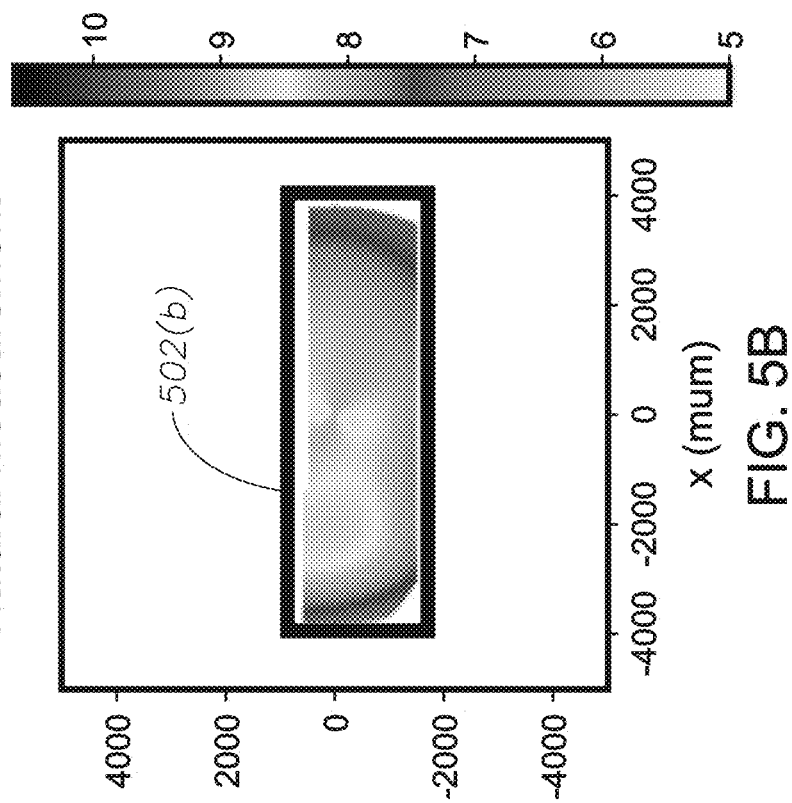
FIGS. 5A-5D are diagrams of corneal topography illustrating changes in ophthalmic measurements during different states of eyelid opening.
Figure 5A:
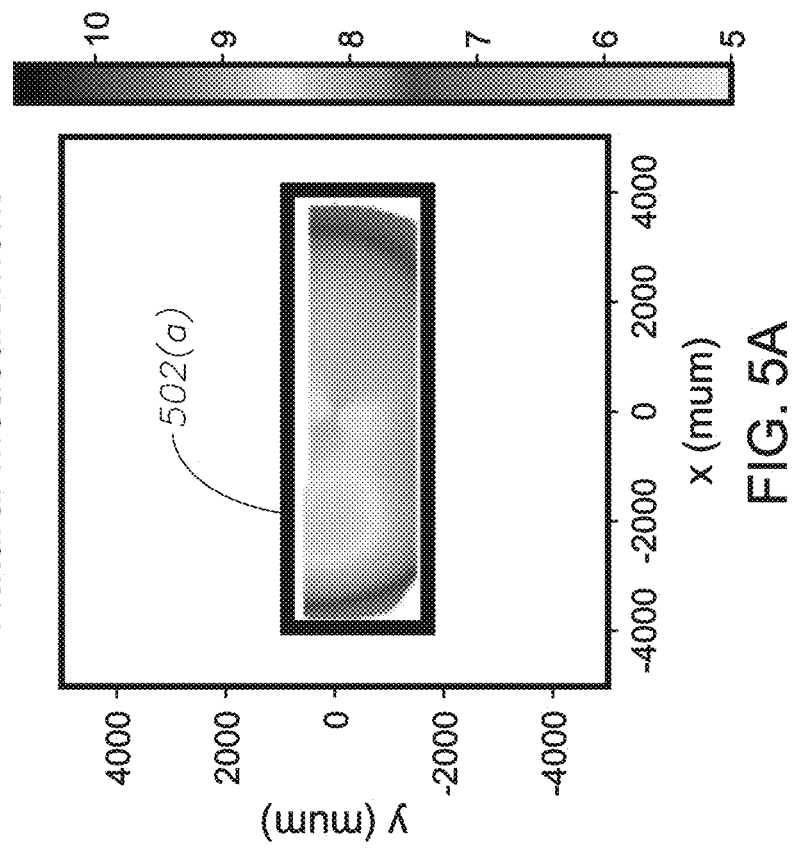
Figure 5D:
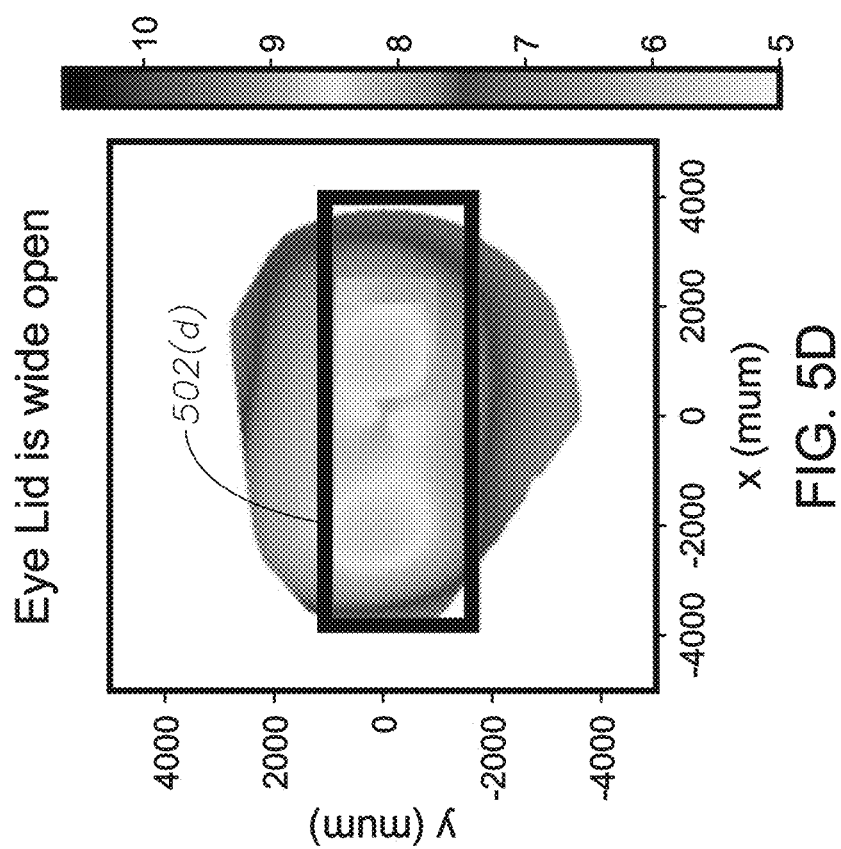
Figure 5C:
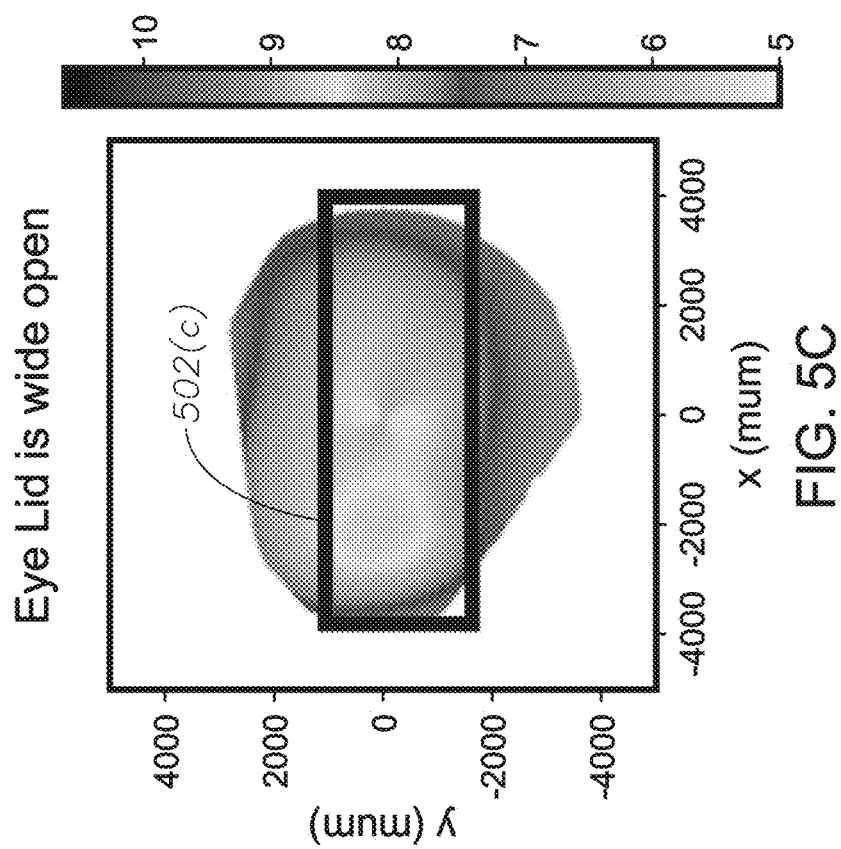

FIGS. 5A-5D are diagrams of corneal topography illustrating changes in ophthalmic measurements during different states of opening of the eyelid 206. FIGS. 5A and 5B illustrate a natural corneal topography where the eyelid 206 is partially closed. A smaller region of coverage is illustrated by box 502(a)-(d). FIG. 5C illustrates a topography map, where the eyelid 206 is wide open as would be the case, for example, when assistance is provided to a patient when opening the eyelid 206. The eye 104 remains in the natural state as the box 502(c) in FIGS. 5C displays measurements similar to the box 502(a) in FIG. 5A. FIG. 5D illustrates corneal topography inside the box 502(d) that has changed relative to the box 502(b) of FIG. 5B indicating that the eye 104 is not in its natural state and deformation of the globe of the eye 104 may be present.

FIGS. 5A and 5C illustrate a comparison where the eye 104 remains in the natural state if the eyelid 206 is being held wide open. The corneal topography region of the natural state is indicated as the box 502(a). The corneal topography of the natural state is similar to the state where the eye is being held open as illustrated by the similarities between the box 502(a) of FIG. 5A and box 502(c) of FIG. 5C. FIGS. 5B and 5D illustrate a case where the corneal topography is different to the natural state if the eyelid 206 is being held open as illustrated by the differences between the box 502(b) and the box 502(d). The eye 104 does not remain in its natural state and deformation of the globe of the eye 104 may be present.

Depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. Although certain computer-implemented tasks are described as being performed by a particular entity, other embodiments are possible in which these tasks are performed by a different entity.

For purposes of this patent application, the term computer-readable storage medium encompasses one or more tangible computer-readable storage media possessing structures. As an example and not by way of limitation, a computer-readable storage medium may include a semiconductor-based or other integrated circuit (IC) (such as, for example, a field-programmable gate array (FPGA) or an application-specific IC (ASIC)), a hard disk, an HDD, a hybrid hard drive (HHD), an optical disc, an optical disc drive (ODD), a magneto-optical disc, a magneto-optical drive, a floppy disk, a floppy disk drive (FDD), magnetic tape, a holographic storage medium, a solid-state drive (SSD), a RAM-drive, a SECURE DIGITAL card, a SECURE DIGITAL drive, a flash memory card, a flash memory drive, or any other suitable tangible computer-readable storage medium or a combination of two or more of these, where appropriate.

The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," "generally," and "about" may be substituted with "within [a percentage] of" what is specified.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices illustrated can be made without departing from the spirit of the disclosure. As will be recognized, the processes described herein can be embodied within a form that does not provide all of the features and benefits set forth herein, as some features can be used or practiced separately from others. The scope of protection is defined by the appended claims rather than by the foregoing description. All changes which come within the meaning and range of equivalency of the claims are to be embraced within their scope.

What is claimed is:

1. A method of verifying ophthalmic measurements, the method comprising:
   obtaining, via an ophthalmic measurement device, a first measurement of at least one ophthalmic parameter, over a first measurement area, the first measurement area corresponding to an unassisted measurable area of a patient's eye, the first measurement area covering less than an entire cornea of the patient's eye;
   obtaining, via the ophthalmic measurement device, a second measurement of the at least one ophthalmic parameter over a second measurement area, the second measurement area corresponding to an assisted measurable area of the patient's eye, wherein the second measurement area includes a sub-region that coincides with the first measurement area, the second measurement area covering the entire cornea;
   obtaining from the ophthalmic measuring device, first reflections associated with the first measurement and second reflections associated with the second measurement;
   sampling a portion of the second measurement corresponding to the sub-region;

comparing the sampled portion of the second measurement to the first measurement comprising scaling the first measurement area to the second measurement area;

determining if the second measurement diverges from the first measurement, the divergence of the second measurement from the first measurement including a difference in the at least one ophthalmic parameter between the first measurement and the second measurement of the at least one ophthalmic parameter;

responsive to a determination that the second measurement diverges from the first measurement, generating an alert that the second measurement is inaccurate;

comparing the first reflections to the second reflections;

determining if there are discrepancies between the first reflections and the second reflections; and responsive to a determination that discrepancies are present between the second reflections and the first reflections, generating an alert that the patient's tear film has dried.

2. The method of claim 1, wherein the ophthalmic parameter is at least one of corneal curvature, axial length, aberrometry, and corneal topography.

3. The method of claim 1, wherein the ophthalmic measurement device is at least one of, a keratometer, an ultrasound biometer, a wavefront device, a topographer, and an aberrometry device.

4. The method of claim 1, wherein the alert is at least one of a visual alert, a textual alert, and an auditory indication.

5. The method of claim 1, comprising:

responsive to a determination that the second measurement diverges from the first measurement, rejecting the second measurement; and repeating the second measurement.

6. The method of claim 5, comprising comparing the repeated second measurement to the first measurement.

7. The method of claim 1, wherein the comparing includes determining a common reference between the first measurement area and the second measurement area.

8. A computer-program product comprising a non-transitory computer-usable medium having computer-readable program code embodied therein, the computer-readable program code adapted to be executed to implement a method comprising:

receiving, from an ophthalmic measurement device, a first measurement of at least one ophthalmic parameter, over a first measurement area, the first measurement area corresponding to an unassisted measurable area of a patient's eye, the first measurement area covering less than an entire cornea of the patient's eye;

receiving, from the ophthalmic measurement device, a second measurement of the at least one ophthalmic parameter over a second measurement area, the second measurement area corresponding to an assisted measurable area of the patient's eye, wherein the second measurement area includes a sub-region that coincides with the first measurement area, the second measurement area covering the entire cornea;

sampling a portion of the second measurement corresponding to the sub-region;

comparing the sampled portion of the second measurement to the first measurement comprising scaling the first measurement area to the second measurement area;

receiving from the ophthalmic measurement device, first reflections associated with the first measurement and second reflections associated with the second measurement;

determining if the second measurement diverges from the first measurement, the divergence of the second measurement from the first measurement including a difference in the at least one ophthalmic parameter between the first measurement and the second measurement of the at least one ophthalmic parameter;

responsive to a determination that the second measurement diverges from the first measurement, generating an alert that the second measurement is inaccurate;

determining if there are discrepancies between the first reflections and the second reflections;

responsive to a determination that discrepancies are present between the second reflections and the first reflections, generating an alert that the patient's tear film has dried; and responsive to a determination that there are no discrepancies between the second reflections and the first reflections, accepting the second measurement as accurate.

9. The computer-program product of claim 8, wherein:

the ophthalmic parameter is at least one of corneal curvature, axial length, aberrometry, and corneal topography; and the ophthalmic measurement device is at least one of a keratometer, an ultrasound biometer, a wavefront device, a topographer, and an aberrometry device.

10. The computer-program product of claim 8, wherein the alert is at least one of a visual alert, a textual alert, and an auditory indication.

11. The computer-program product of claim 8, comprising:

responsive to a determination that the second measurement diverges from the first measurement, rejecting the second measurement;

repeating the second measurement, and comparing the repeated second measurement to the first measurement.

12. The computer-program product of claim 8, wherein the comparing includes determining a common reference between the first measurement area and the second measurement area.

* * * * *